United States Patent [19]
Feeman et al.

[11] Patent Number: 5,735,941
[45] Date of Patent: Apr. 7, 1998

[54] INK SYSTEM WITH REDUCED BLEED

[75] Inventors: James F. Feeman, Wyomissing, Pa.; Ann P. Holloway, Lexington, Ky.; Agnes K. Zimmer, Lexington, Ky.; Jing X. Sun, Lexington, Ky.; Terence E. Franey, Lexington, Ky.; James M. Mrvos, Lexington, Ky.; Bradley L. Beach, Lexington, Ky.

[73] Assignee: Lexmark International, Inc., Lexington, Ky.

[21] Appl. No.: 690,468

[22] Filed: Jul. 24, 1996

[51] Int. Cl.$^6$ .................................... C09D 11/02
[52] U.S. Cl. .................... 106/31.28; 106/31.43; 106/31.49; 106/31.51; 106/31.52; 106/31.48; 106/31.5; 106/31.6
[58] Field of Search ................ 106/31.28, 31.43, 106/31.49, 31.51, 31.52, 31.48, 31.5, 31.6

[56] References Cited

U.S. PATENT DOCUMENTS

| | | | |
|---|---|---|---|
| 3,852,029 | 12/1974 | Bolliger et al. | 8/527 |
| 3,889,271 | 6/1975 | Freytag et al. | 106/31.46 |
| 4,533,920 | 8/1985 | Suzuki | 106/31.27 |
| 4,554,555 | 11/1985 | Aruga et al. | 106/31.43 |
| 4,581,036 | 4/1986 | Opitz et al. | 8/527 |
| 4,694,302 | 9/1987 | Hackleman et al. | 106/31.37 |
| 4,963,189 | 10/1990 | Hindagolla | 106/31.52 |
| 5,025,271 | 6/1991 | Baker et al. | 347/87 |
| 5,062,893 | 11/1991 | Adamic et al. | 106/31.52 |
| 5,106,416 | 4/1992 | Moffatt et al. | 106/31.43 |
| 5,156,675 | 10/1992 | Breton et al. | 106/31.43 |
| 5,160,372 | 11/1992 | Matrick | 106/31.43 |
| 5,181,045 | 1/1993 | Shields et al. | 106/31.27 |
| 5,183,501 | 2/1993 | Kawashita et al. | 106/31.44 |
| 5,196,056 | 3/1993 | Prasad | 106/31.58 |
| 5,198,023 | 3/1993 | Stoffel | 106/31.32 |
| 5,207,824 | 5/1993 | Moffatt et al. | 106/31.46 |
| 5,226,957 | 7/1993 | Wickramanayake et al. | 106/31.26 |
| 5,320,668 | 6/1994 | Shields et al. | 106/31.28 |
| 5,342,439 | 8/1994 | Lauw | 106/31.43 |
| 5,342,440 | 8/1994 | Wickramanayake | 106/31.43 |
| 5,364,461 | 11/1994 | Beach et al. | 106/31.58 |
| 5,401,303 | 3/1995 | Stoffel et al. | 106/31.43 |
| 5,428,383 | 6/1995 | Shields et al. | 106/31.27 |
| 5,476,540 | 12/1995 | Shields et al. | 106/31.36 |
| 5,518,534 | 5/1996 | Pearlstein et al. | 106/31.75 |
| 5,531,816 | 7/1996 | Wickramanayake | 106/31.78 |
| 5,604,276 | 2/1997 | Suga | 106/31.28 |

FOREIGN PATENT DOCUMENTS

0633142A1  1/1995  European Pat. Off.

*Primary Examiner*—Helene Klemanski

[57] ABSTRACT

An ink system comprising a first ink containing a flocculating dye in an aqueous solution and a second ink containing a dispersant-pigment complex in an aqueous solution reduces bleed between the two inks when they are applied side by side. The flocculating dye flocculates the dispersant-pigment complex

37 Claims, No Drawings

INK SYSTEM WITH REDUCED BLEED

TECHNICAL FIELD

The present invention relates generally to ink employed in ink-jet printing. More particularly, it is directed to a system of black and colored inks in which color bleed is substantially reduced or eliminated.

BACKGROUND OF THE INVENTION

Ink jet printing is accomplished by ejecting ink from a nozzle toward paper or another print medium. The ink is driven from the nozzle toward the medium in a variety of ways. For example, in electrostatic printing, the ink is driven by an electrostatic field. Another ink jet printing procedure, known as squeeze tube, employs a piezoelectric element in the ink nozzle. Electrically-caused distortions of the piezoelectric element pump the ink through the nozzle and toward the print medium. In still another ink jet printing procedure, known as thermal or bubble ink jet printing, the ink is driven from the nozzle toward the print medium by the formation of an expanding vapor phase bubble in the nozzle. These various printing methods are described in "Output Hard Copy Devices," edited by Durbeck and Sherr, Academic Press, 1988 (see particularly chapter 13, entitled "Ink Jet Printing").

Preferably, an ink jet printer is capable of printing with colored ink, such as magenta, cyan and yellow, as well as black ink. When two colors are printed side by side, particularly when black ink is printed next to any other colored ink, the colors can "bleed" into one another. "Bleed" is defined as the migration of one ink color into a region of another ink color, particularly when black ink moves into a region of any other color. It is desirable to have a clean, crisp border between areas of two different colors. When one color bleeds into the other color, the border becomes irregular and ragged.

Bleed is particularly undesirable when black ink is printed next to a light color ink, such as yellow.

Numerous methods have been developed in an attempt to reduce or eliminate the bleed between different colors of ink, particularly the bleed between black ink and colored ink.

One method to reduce bleed between inks is to incorporate one anionic ink and one cationic ink as disclosed in European Patent 633,142, Stoffel, et al., published Jan. 11, 1995. Both the anionic and cationic inks are aqueous solutions and contain a colorant which may be either a pigment or a dye. In one of the two inks, a polymer must be added which is of the same ionic character as the ink in which it is incorporated.

Cationic dyes are also disclosed in U.S. Pat. No. 5,198,023, Stoffel, issued Mar. 30, 1993. In this patent, a cationic yellow dye is used with an anionic black dye. Bleed is further reduced by adding a multivalent precipitating agent to the yellow ink. This multivalent precipitating agent is typically a multivalent salt, such as calcium chloride, magnesium chloride and aluminum chloride.

Bleed can also be alleviated by using pH sensitive dyes. U.S. Pat. No. 5,181,045, Shields, et al., issued Jan. 19, 1993, describes the use of a dye which is rendered insoluble by contacting -it with another ink of the proper pH. This reaction occurs at the border of the two inks and is distinguished from systems where the pH of the paper is used to render the dyes insoluble. The pH of the second ink can be either higher or lower than that of the first ink. However, the pH difference should be greater than one unit. The '045 patent discloses dyes with proper pH. U.S. Pat. No. 5,320,668, Shields, et al., issued Jun. 14, 1994, which is a continuation in part of the '045 patent, discloses not only dyes but inks containing either pigments or dyes.

Color bleed is controlled by employing zwitterionic surfactants or ionic or non-ionic amphiphiles according to the teachings of U.S. Pat. No. 5,106,416, Moffat, et al., issued Apr. 21, 1992. The inks described contain one or more cationic dyes.

Bleed resistance is increased in dyes by counter-ion substitution in U.S., Pat. No. 5,342,439, Lauw, issued Aug. 30, 1994. A dye having one or more sulfonate or carboxylate groups is provided with a counter-ion comprising an mine, which is used for its surfactant properties. Such a dye is produced in an ionic exchange process.

The use of precipitating agents is taught in U.S. Pat. No. 5,428,383, Shields, et al, issued Jun. 27, 1995. Color bleed between two ink compositions is controlled by incorporating a precipitating agent in the second ink which precipitates the first ink coloring agent. When the two ink compositions contact each other on the paper, a precipitate is formed which prevents migration and color bleed problems.

In U.S. Pat. No. 4,694,302, Hackleman, et al., issued Sep. 15, 1987, the ink includes a reactive species which forms a polymer when the ink hits the paper. The reactive species either reacts with a component in the substrate, i.e., the paper, or alternatively reacts with a material which is applied to the substrate before the ink is applied.

U.S. Pat. No. 5,476,540, Shields, et al., Dec. 19, 1995, teaches the use of gel forming inks to alleviate bleed. In such a system, one ink contains a gel forming species and the other ink contains a gel initiating species, typically a protonated tertiary amine. When the two inks come in contact with each other, gel is formed, thereby preventing movement of the coloring agent.

Micro-emulsions comprising water insoluble black dyes are also used to prevent bleed between the black ink and the colored ink. Such inks are taught in U.S. Pat. Nos. 5,342,440, Wickramanayake, issued August 30, 1994, and 5,226,957, Wick ramanayake, et al, Jul. 13, 1993. In each case the black dyes are water insoluble. They are used in conjunction with colored inks that contain water soluble dyes. The water insoluble black dyes will not migrate through the water based color inks and, thus, bleed is prevented.

Bleed is also controlled by adding additional agents to the ink composition. For example, in U.S. Pat. No. 5,196,056, Prasad, issued Mar. 23, 1993, a bleed retarding agent which has a polar portion and a non-polar portion is added to the ink. A particularly preferred bleed retarding agent is 2-(2-butoxyethoxy) ethanol. In U.S. Pat. No. 5,160,372, Matrick, issued Nov. 3, 1992, an ester or amide diol is added to the ink to improve the penetration of the ink into the paper. This also provides rapid drying.

The instant invention is directed to an ink system, and a method of reducing or eliminating bleed in ink systems without requiring the addition of other materials to the inks. The invention employs a flocculating dye in a first ink which acts as a flocculant to a dispersed segment of a second ink in its proximity.

SUMMARY OF THE INVENTION

In a fast aspect, the present invention provides an ink system comprising:

a. a first aqueous ink comprising a flocculating dye; and
b. a second aqueous ink comprising a dispersant-pigment complex.

wherein the flocculating dye of said first ink is capable of flocculating the dispersant-pigment complex of said second ink.

In a second aspect, the present invention further provides a method of controlling bleed between inks of different colors comprising the steps of:

a. applying a first aqueous ink comprising a flocculating dye; and b. applying a second aqueous ink comprising a dispersant-pigment complex, wherein the first ink and second ink are applied one before the other or simultaneously, the flocculating dye of said first ink is capable of flocculating the dispersant-pigment complex of said second ink and the first ink and second ink are applied contiguous to one another.

It has been unexpectedly discovered in this invention that color bleed in the ink system of this invention is substantially eliminated without requiring the use of additional cationic materials in the aqueous ink comprising flocculating dye. For example, the presence of metal cations like Group IIA, IIIA and IIIB metal cations [as defined by The Periodic Table of Elements in the Handbook of Chemistry and Physics, 55th Edition, 1974–1975] are not required.

Furthermore, it is noted herein that when a cationic group is present on a dye compound, there will also be a counter anion present. Illustrative examples of such anionic groups include monoalkylsulfates or halides.

DETAILED DESCRIPTION OF THE PREFERRED EMBODIMENT

Ink system as used herein is defined to mean an ink set which comprises at least two (preferably differently colored) inks. At least one ink comprises a flocculating dye and typically does not have any dispersants or pigments, and at least one ink comprises a dispersant-pigment complex and typically does not have a flocculating dye. The ink system exists when the ink comprising the flocculating dye and the ink comprising the dispersant-pigment complex are sold together as original components in an ink jet printer. The system also exists when the inks are sold separately as replacement cartridges or refills for cartridges with instructions for the inks to be used in conjunction with one another.

The ink system of the present invention often comprises two inks wherein a first ink comprises a flocculating dye and a second ink comprises a dispersant-pigment complex. The dye acts as a flocculating agent with respect to the dispersant-pigment complex, causing the dispersant-pigment complex to agglomerate when the first ink comes into contact with the second ink. Such agglomeration/flocculation, prevents bleed (color contamination) between colors after printing on a substrate.

Dispersant-pigment complex is defined herein to mean that the dispersant stabilizes the pigment by surrounding the pigment (in a micelle like fashion), thereby preventing it from flocculating.

Flocculating dye as used herein is defined as a dye molecule that 1) has at least one cationic functional group, i.e., a group that exhibits a positive charge, 2) is capable of flocculating a dispersant-pigment complex in a second ink, and 3) exhibits sufficient solubility in water to be used in ink jet ink applications.

The flocculating dyes which may be employed in this invention are generally not limited and include, for example, commercially available cationic dyes, also called basic dyes, as well as the novel compounds described in U.S. patent application LE9-96-020, the disclosure of which is incorporated herein by reference. For clarification purposes, the terms "basic" and "cationic" may be used interchangeably. Commercial dyes, which meet the three criteria of a flocculating dye, as previously defined, may be used in the present invention, whether they are identified as basic or cationic. Further, it is noted that the cationic charge can be pendant, i.e., insulated from the chromogenic part of the dye, or delocalized, wherein a cationic charge is delocalized in the chromogen. Commercially available cationic dyes which may be employed in this invention include basic dyes listed in the Color Index. Illustrative examples include the basic dyes described in European Patent Application 608,429 published Aug. 3, 1994, and incorporated herein by reference. Additional dyes include cationic dyes derived from anthraquinone, diphenylmethane, triphenylmethane, acridine, pyran, thiopyran, indamine, azine, oxazine, thiazine, hemicyanine, azacarbocyanine, diazacarbocyanine, triazacarbocyanine and diazahemicyanine as well as dyes which may be classified as cationic azo type dyes. Preferred commercial dyes which may be employed in this invention are C.I. Basic Yellow 45, C.I. Basic Blue 163, C.I. Basic Red 15, C.I. Basic Red 16 or C.I. Basic Red 49.

Other preferred dyes which may be employed in this invention include the above-mentioned novel compounds described in U.S. patent application LE9-96-020, which again, has been incorporated herein by reference. Such novel compounds are made via a variety of methods which include, for example, additions and/or nucleophilic substitution reactions as well quarternizations, condensations and diazotizations and combinations thereof. More detailed descriptions of the preparation of the novel compounds which may be employed in this invention are described in the examples which later follow.

The novel compounds that are suitable for use in the present invention include those represented by the formula:

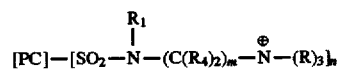

wherein m is about 0–6; n is about 2–4; each R is independently lower ($C_{1-4}$) alkyl, arylalkyl or hydroxyalkyl; PC is a metallic or nonmetallic comprising phthalocyanine group, wherein a metallic group is present, it is preferably a transition metal such as nickel, but preferably copper, and $R_1$ is H or $CH_3$; and each $R_4$ is independently H, lower alkyl or hydroxyalkyl.

Preferably, the above compound is a cyan dye and selected from the group consisting of:

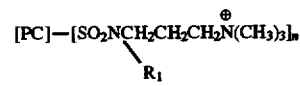

and

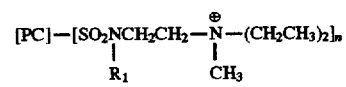

wherein $R_1$ is H or —$CH_3$ and n is about 3 or 4.

A second novel compound which may be employed in this invention is represented by the formula:

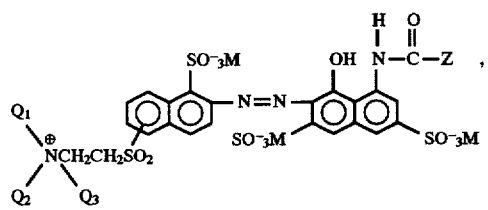
wherein $Q_1$ is hydroxyalkyl or
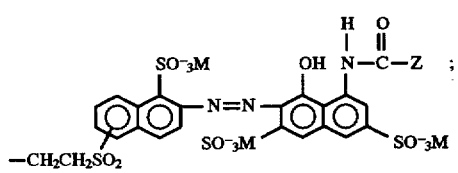
$Q_2$ is H, lower alkyl,
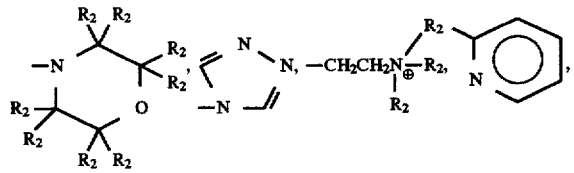
-continued
hydroxyalkyl,
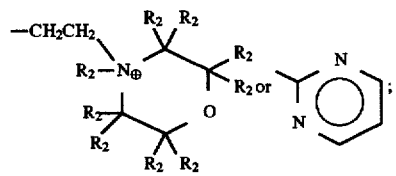
$Q_3$ is H or $(C_{1-4})$ alkyl;
each M is independently $H^+$, $Na^+$, $K^+$, $Li^+$, $N^+(R_2)_4$;
each $R_2$ is independently H, lower $(C_{1-4})$ alkyl or hydroxyalkyl Z is an aromatic, aliphatic, amine or alkoxy group.
Preferably the second novel compound is a magenta dye selected from the group consisting of:
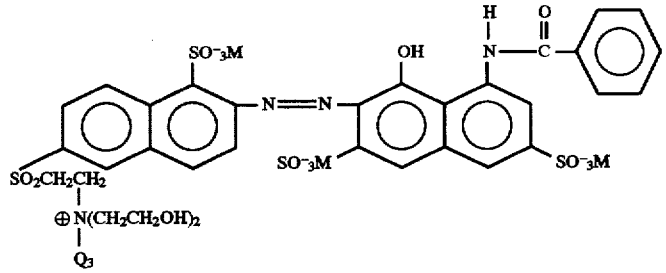
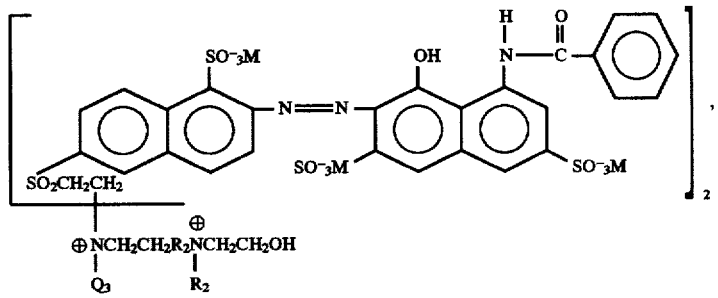

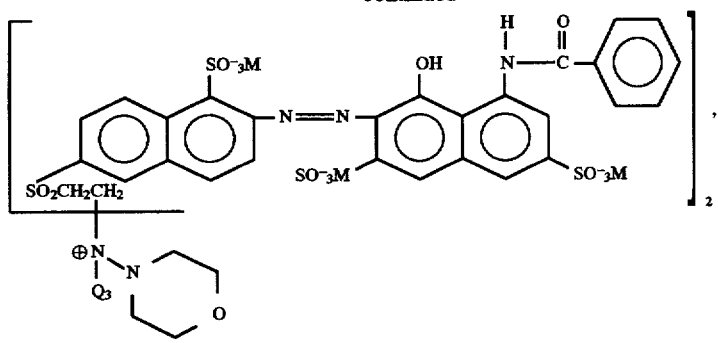
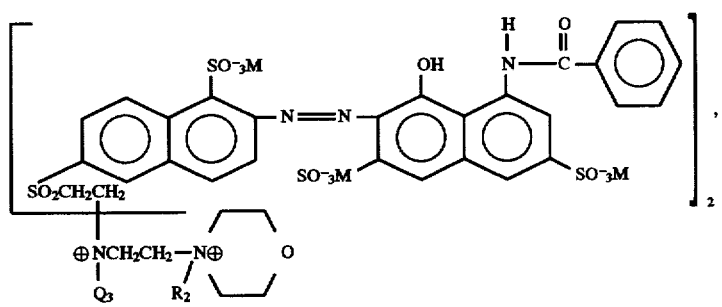
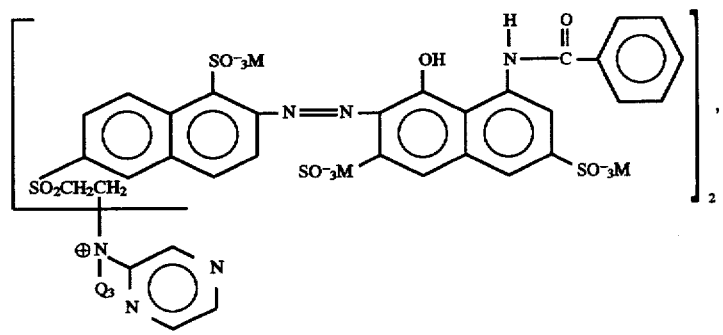
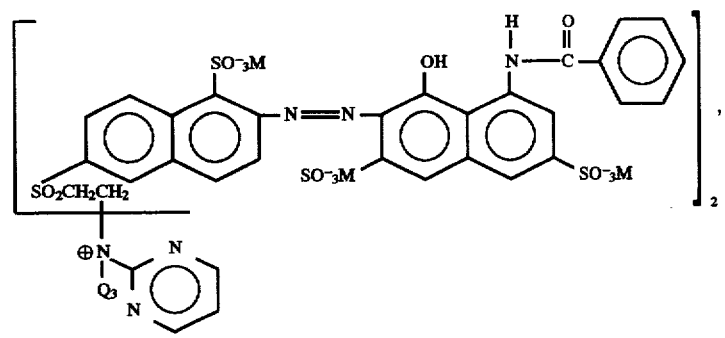
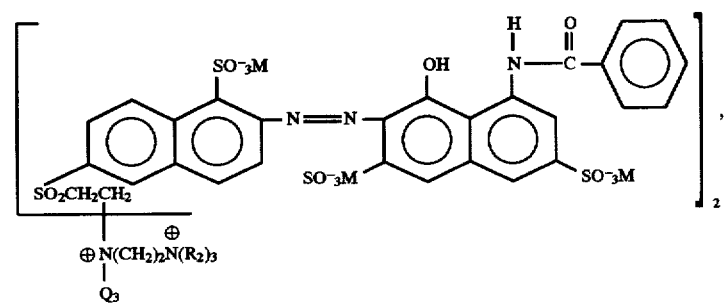

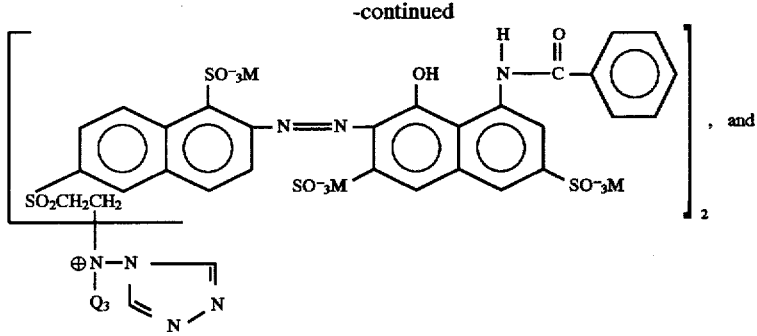
, and
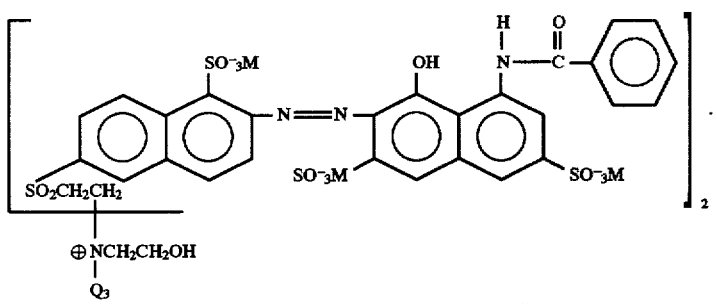
.
Most preferably the second novel compound is a magenta dye having the formula:
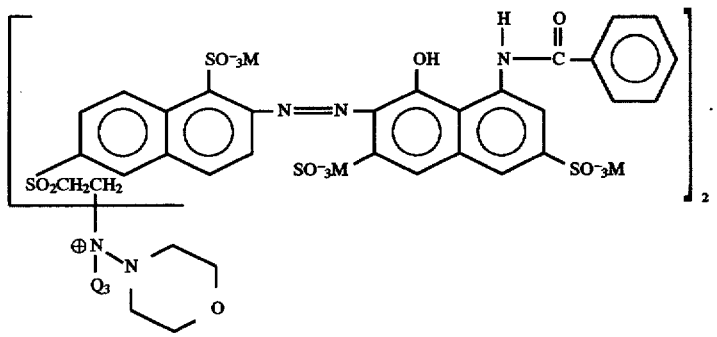
.
Additional novel compounds which may be employed include those having the formula:
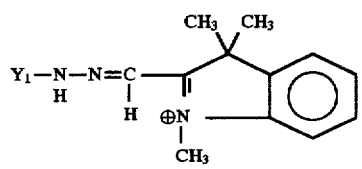
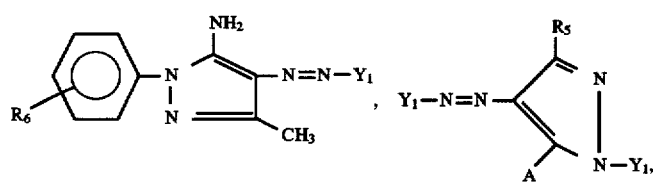

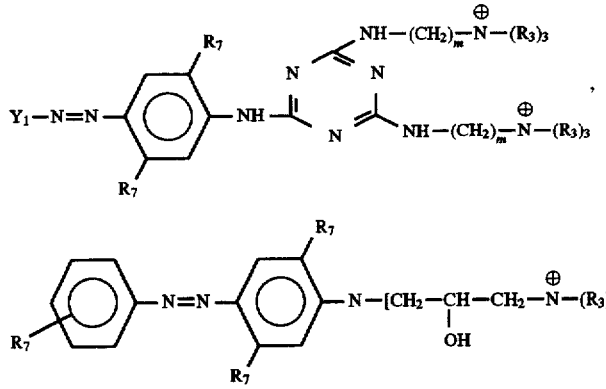

wherein each m is independently about 0 to 6;
m' is about 0 to 6;
each $R_3$ is independently a $(C_{1-4})$ alkyl or hydroxyalkyl
$R_5$ is a $(C_{1-4})$ alkyl or —$CO_2M$;
$R_6$ is H, halogen, $(C_{1-4})$ alkyl or $(C_{1-4})$ alkoxyl;
each $R_7$ is independently H, halogen, lower alkyl or lower alkoxyl;

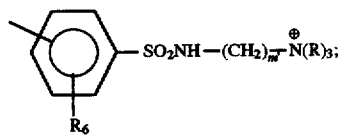

A is —OH or —$NH_2$; and
M is as previously defined.

Preferably the additional novel compounds are yellow dyes selected from the group consisting of:

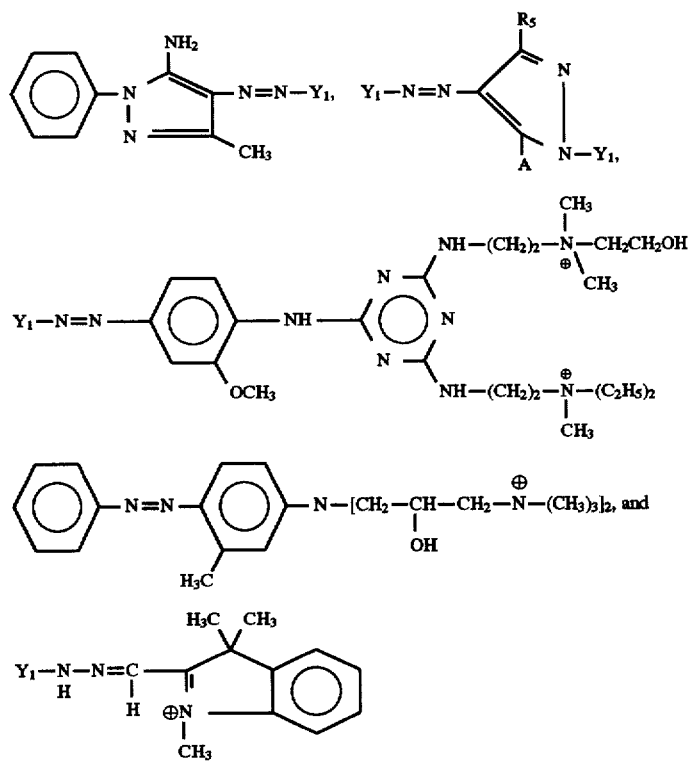

wherein R is —$CH_3$ and m' is 3.

Still other novel compounds include those selected from a group consisting of:

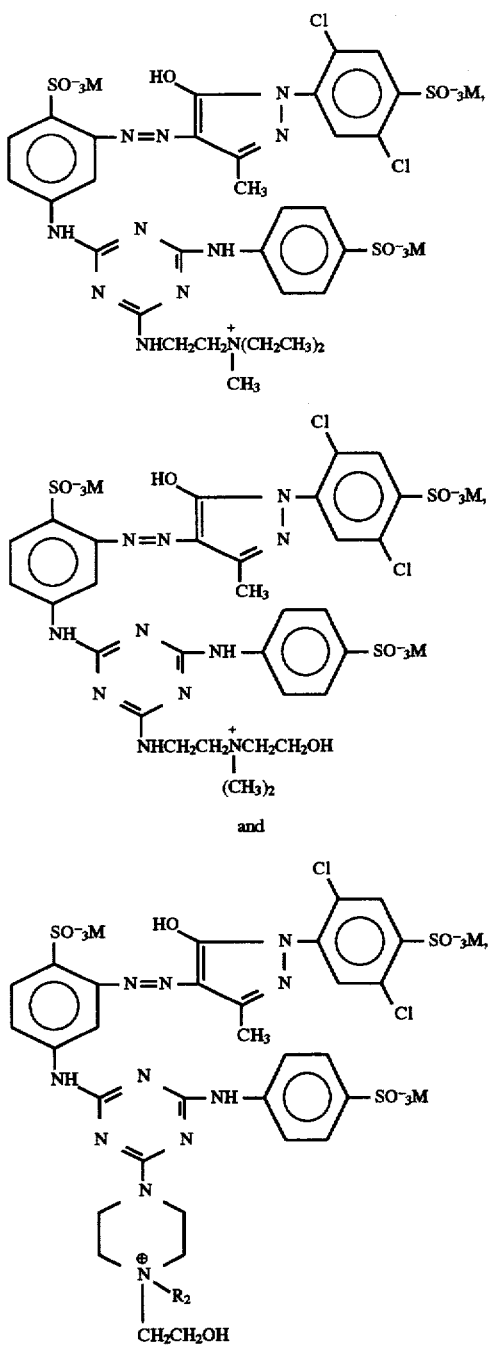

and wherein each M is independently $H^\oplus$, $Na^\oplus$, $K^\oplus$, $Li^\oplus$, $N^\oplus(R_2)_4$, each $R_2$ is independently H, ($C_{1-4}$) alkyl or hydroxyalkyl; and wherein the compounds may generally be classified as yellow dyes which may be prepared from C.I. Reactive Yellow 2.

There is generally no limitation with respect to how the first aqueous ink employed in the instant invention is made. Often, a dried dye is added to a solvent or an aqueous solution. Additional methods include adding a dye solution which is miscible in the solvent or aqueous solution. Any typical ink additives like, for instance, humectants may be added to the solvent or aqueous solution wherein conventional steps like heating and mixing may be employed to enhance ink formation.

The preferred solvent employed in the first aqueous ink is deionized water, and the most preferred aqueous solution is one which comprises deionized water.

The first aqueous ink often comprises from about 0.1 to about 12.0 weight percent dye based on total weight of the first aqueous ink, including all ranges subsumed therein. Preferably the first ink comprises from about 0.25 to about 10.0 weight percent dye and most preferably from about 0.5 to about 5.0 weight percent dye based on total weight of the first aqueous ink, including all ranges subsumed therein.

Often preferred additives which may be employed in the first aqueous ink of this invention include humectants, penetrants and biocides. Other optional additives which may be employed include additional cationic materials.

The humectants which may be employed in this invention are generally not limited and are known in the art. Illustrative examples include alkylene glycols like diethylene glycol, triethylene glycol, tetraethylene glycol and polyethylene glycols as well as diols such as 1,2-propanediol and 1,2-butanediol.

The penetrants, which may be employed in this invention are generally not limited and includes hydroxy substituted hydrocarbons like 1,2-alkyl diols such as 1,2-pentanediol, 1,2-hexanedoil and mixtures thereof. A more detailed description of such penetrants may be found in U.S. Pat. No. 5,364,461, Beach, et al., issued Nov. 15, 1994, incorporated herein by reference. The optional cationic materials which may be employed in the first aqueous ink of this invention act as secondary flocculating agents, in addition to the flocculating dye, helping to agglomerate the dispersant-pigment complex of the second aqueous ink, thereby further reducing bleed after the inks are applied to a substrate. Any positively charged material that is capable of flocculating the dispersant-pigment complex may, if desired, act as an additional cationic material. Suitable materials include commercially available quaternary amines, tertiary amines and secondary amines. Preferably, the additional cationic material is a quaternary amine like 1-dodecylpyridinium chloride and 1-hexadecylpyridinium chloride.

Other suitable quaternary amines include compounds with the following structures:

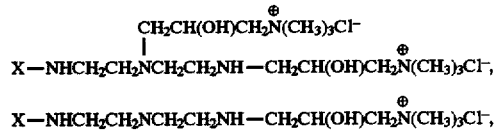

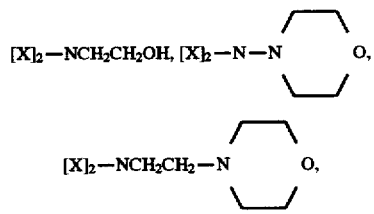

wherein X is Cl⁻(CH₃)₃N⁺CH₂CH(OH)CH₂,

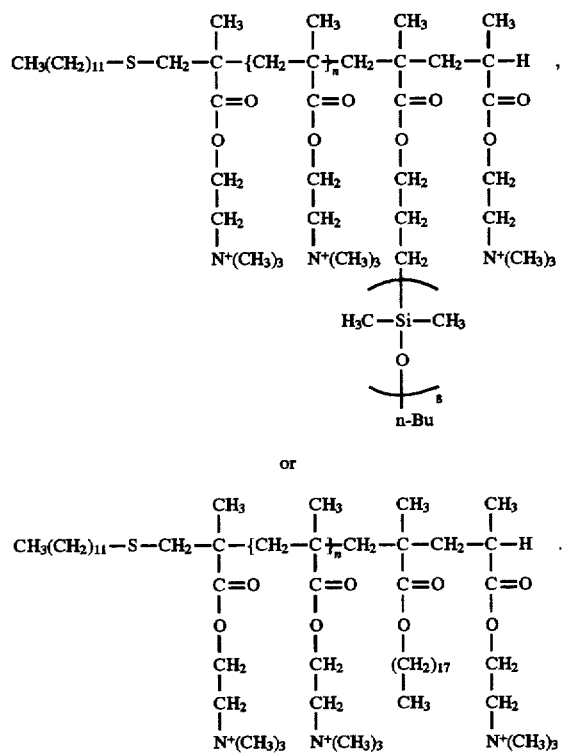

These types of compounds are prepared, for example, by reacting corresponding amine compounds with (3-chloro-2-hydroxypropyl) trimethylammonium chloride, wherein their preparation will be further addressed in the examples which follow.

The biocides which may be employed are known and commercially available. They prevent growth of microorganisms in the ink. Examples of biocides that are suitable for use in this invention include those, for instance, which comprise benz-isothiazolin-one, methyl-isothiazolin-one and chloro-methyl-isothiazolin-one.

Often the first aqueous ink has a pH below about 7. It is more preferable that the pH be between about 4 and about 6. The pH can be obtained by adding either a base or an acid to the prepared first aqueous ink as necessary to adjust the pH. Appropriate acids and bases are well known in the art. Should it be necessary to add a base, the base preferably is sodium hydroxide. Should it be necessary to add an acid, the acid preferably is glycolic acid.

Often, in this invention, the first aqueous ink is about 0.5 to about 5.0 weight percent flocculating dye, about 5.0 to about 25% by weight percent humectant, about 0.05 to about 10% by weight penetrant, 0.0 to about 5.0 weight percent additional cationic material and about 0.1 to about 0.5 weight percent biocide based on total weight of the first aqueous ink, with any balance being deionized water.

In general, all of the conventional process steps may be employed when making the second aqueous inks, including heating and stirring.

The second aqueous ink, therefore, is a solution comprising a dispersant-pigment complex. The second aqueous ink often comprises about 1.0 to about 12.0 weight percent dispersant-pigment complex based on total weight of the second aqueous ink. Preferably, the second aqueous ink comprises from about 2.0 to about 4.0 weight percent dispersant-pigment complex based on total weight of the second aqueous ink.

The amount of dispersant to pigment in the dispersant-pigment complex is generally limited only to the extent that the second aqueous ink may be formed. The dispersant to pigment ratio often, however, ranges from about 1:1 to about 6:1, depending upon the dispersants and pigments which are employed.

There is essentially no limitation to the pigments which may be employed. Typical examples of pigments which may be used in the present invention include dye lakes, azo pigments including condensed azo pigments, and chelate azo pigments; polycyclic pigments, such as phthalocyanine pigments, anthraquinone pigments, quinacridone pigments, dioxazine pigments, thioindigo pigments, isoindolinone pigments, and quinophthalone pigments. Other pigments include nitro pigments, nitroso pigments and daylight fluorescent pigments as well as titanium dioxide, iron oxide, aniline black and carbon black. Preferred pigments for use in the present invention are titanium dioxide, iron oxide and carbon black. Most preferably, the pigment is carbon black.

The polymeric dispersants useful in this invention are generally not limited and include any of those capable of dispersing, for example, pigments such as carbon black. The dispersants typically comprise hydrophobic and hydrophilic polymeric segments. The hydrophobic segment tends to interact with the pigment particular in the second aqueous ink and the hydrophilic segments tend to be solvated by the aqueous medium thereby dispersing the pigment (as defined herein as the dispersant-pigment complex).

Illustrative examples of the dispersants which may be employed in this invention include AB, BAB and ABC block copolymers known in the art. Preferred AB and BAB block copolymers include those, for example, which comprise hydrophobic and hydrophilic segments derived from acrylic monomers. Such dispersants are further described in U.S. Pat. No. 5,085,698, the disclosure of which is incorporated herein by reference.

A most preferred class of dispersants which may be employed in the present invention include block and/or graft co- or terpolymers comprising a hydrophilic polymeric segment, and one or two hydrophobic polymeric segment(s) having a hydrolytically stable siloxyl substituent or a hydrophobic amide side chain. A particularly preferred subgroup of these dispersants are graft terpolymers which comprise a hydrophilic polymeric segment (particularly an acrylic or methacrylic acid co- or terpolymer) together with a hydrophobic polymeric segment derived from a polyorganosiloxane as described in U.S. patent application Ser. No. 08/360,199, filed Dec. 21, 1994 and incorporated herein be reference.

Another group of polymeric dispersants include those described in U.S. patent application Ser. No. 08/360,200, filed Dec. 21, 1994 and incorporated herein by reference. These materials are graft polymers which comprise a hydrophilic polyacrylic acid backbone of weight average molecular weight between about 1,000 and about 5,000, and hydrophobic segment side chains randomly grafted to the backbone.

Often at least about 0.5% and no more than about 50% of all reactive sites on the polymer backbone have grafted thereon one of the structural units described above.

Still another polymeric dispersant which may be employed in this invention is one derived from an amine comprising polymer and a hydrophobic segment having acid functionality. These dispersants have also been described in U.S. patent application Ser. No. 08/360,200 which, again, has been incorporated herein by reference.

It is also noted herein that the second aqueous ink may comprise a second solvent such as an organic solvent which is miscible with deionized water. Selection of a suitable deionized water miscible solvent depends on the requirements of the specific aqueous ink being formulated, such as the desired surface tension and viscosity, the pigment being used, the drying time required for the pigmented ink, and the type of paper onto which the ink will be printed. Representative examples of water soluble organic solvents that may be selected include (1) alcohols, such as methyl alcohol, ethyl alcohol, n-propyl alcohol, iso-propyl alcohol, n-butyl alcohol, sec-buty alcohol, t-butyl alcohol, iso-butyl alcohol, furfuryl alcohol, and tetrahydrofurfuryl alcohol; (2) ketones or keto alcohols, such as acetone, methyl ethyl ketone, and diacetone alcohol; (3) ethers, such as tetrahydrofuran and dioxane; (4) esters, such as ethyl acetate, ethyl lactate, ethylene carbonate and propylene carbonate; (5) polyhydric alcohols, such as ethylene glycol, diethylene glycol, glycerol, 2-methyl-2,4-pentanediol, 1,2,6-hexanetriol and thiodiglycol; (6) lower alkyl mono- or di-ethers derived from alkylene glycols, such as ethylene glycol monomethyl (or monoethyl) ether, diethylene glycol monomethyl (or monoethyl) ether, propylene glycol monomethyl (or monoethyl) ether, triethylene glycol monomethyl (or monoethyl) ether and diethylene glycol dimethyl (or diethyl) ether; (7) nitrogen-containing cyclic compounds, such as pyrrolidone, N-methyl-2-pyrrolidone, and 1,3-dimethyl-2-imidazolidinone; and (8) sulfur-containing compounds, such as dimethyl sulfoxide and tetramethylene sulfone. Other useful solvents include lactones and lactams.

When miscible mixtures of water and an organic solvent are used as the solvent for the second aqueous ink, the mixtures usually comprise greater than about 25% by weight water to about 99.9% by weight water based on total weight of the mixture. The preferred weight percent of deionized water employed is about 50% to about 99.9% based on total weight of the mixture.

The second ink composition of the present invention may be prepared by any method known in the art for making such compositions. The key aspect of the composition is that the pigment and polymeric dispersant form a stable dispersion in the second ink solvent. In one method, the pigment and polymeric dispersant are first mixed together, then milled in an attritor to reduce the particle size to an acceptable level. This material is then blended with the other ink components. Optionally, a surfactant may be added to enhance the pigment dispersion and modify the surface tension of the ink to control its penetration into the paper. Suitable surfactants include nonionic, amphoteric and ionic surfactants. Like the first ink composition, other additives such as biocides, humectants, chelating agents, and viscosity modifiers, may be added at their art established levels to achieve their art known benefits. It generally is desirable to make the pigmented ink jet ink in concentrated form to enhance pigment dispersion. The ink is then subsequently diluted to the appropriate concentration for use in the ink jet printing system.

The first and second ink of this invention are made available as an ink system. This system can comprise the first and second inks sold together as a kit. This kit exists when the two inks are sold together as original components in a new printer. The kit comprising the two inks can also be sold as replacement cartridges. The system also comprises the first ink that is sold individually as a replacement cartridge with instructions that it be used in conjunction with the second ink. Similarly, the system comprises the second ink sold individually as a replacement cartridge with instructions that it be used with the first ink.

The two inks of the ink system can be applied to the substrate so that the first ink and the second ink contact one another along at least one border. They can be applied to the substrate in any order, essentially simultaneously, or one ink can be applied after the other ink has substantially dried on the substrate.

The following examples are detailed descriptions of methods of preparation and use of the inks and the ink system of the present invention. The detailed descriptions fall within the scope of, and serve to exemplify, the more general description set forth above. These examples are presented for illustrative purposes only, and not intended as a restriction on the scope of the invention.

EXAMPLE 1

The dye intermediate N'-(3-dimethylaminopropyl)-sulfanilamide having the structure:

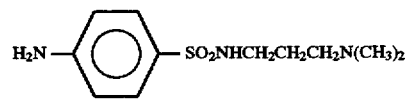

is prepared as follows: 3-Dimethylaminopropylamine (105 g, 1 mole) is dissolved in 500 mL water, cooled with 500 g ice, and with good stirring treated with 239 g N-acetylsulfanilyl chloride during about 15 minutes. The pH is allowed to drop to 7 during another 10 minutes, when the mixture becomes viscous. The pH is raised to about 11.5 and maintained there by adding 50% sodium hydroxide solution (160 g) as required until the reaction is complete, resulting in complete solution. The temperature is allowed to rise to 20° C. After an additional hour during which a clear solution forms, hydrolysis of the acetyl group is effected by adding 100 g of 50% sodium hydroxide solution and heating at 90° C. for three hours. Cooling to room temperature, and neutralizing with hydrochloric acid to pH 9.5 gives an oily precipitate, which soon crystallizes. The product is collected, dried and recrystallized from isopropanol, giving a high yield of product having the desired structure as confirmed by NMR spectroscopy.

EXAMPLE 2

The yellow dye having the structure:

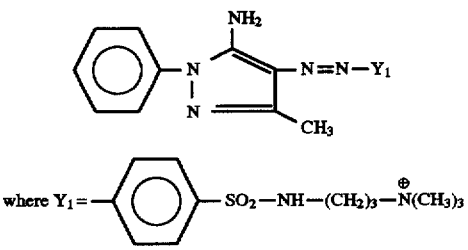

is prepared by diazotizing the intermediate prepared in Example 1 and coupling with 1-phenyl-3-methyl-5-aminopyrazole, then converting the dimethylamino group to trimethylammonium by reaction of the resultant azo intermediate with dimethyl sulfate in aqueous solution. N'-(3-dimethylaminopropyl)-sulfanilamide (6.44 g) is dissolved in 25 mL water with 7 mL 37% hydrochloric acid, iced to 0° C. and diazotized by adding a solution of 1.75 g of sodium nitrite in 5 mL water. Excess nitrite is removed with a small amount of sulfamic acid. To the stirring diazonium salt solution is added 4.4 g of 1-phenyl-3-methyl-5-aminopyrazole which is allowed to dissolve and couple. The reaction is diluted with 100 mL water and the pH slowly

19 raised by dropping in 28 g 3N NaOH. The product precipitates but begins to redissolve as the pH rises. Further sodium hydroxide (50 g, 3N) is added, followed by 4 g dimethyl sulfate. A yellow solution forms. After stirring for 1 hour, the pH is lowered to 9.5 by addition of sodium bicarbonate and a yellow oily layer forms, which is separated by decanting. This is redissolved in deionized water (50 mL) with adjustment of the pH to 5.5. The volume is made up to 110 mL with water, giving an approximately 10% solution of a bright lemon-yellow cationic dye suitable for use in making inks for ink-jet printing. Prints prepared from ink made from this dye had excellent wet-fastness on paper.

EXAMPLE 3

Preparation of pyrazolone from N'-(3-dimethylaminopropyl)-sulfanilamide having the structure:

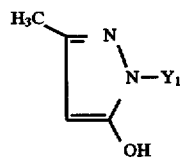

A solution of 0.2 g mole (51.5 g) of the intermediate prepared as in Example 1 in 215 mL water, is iced to 0° C., and stirred in an ice bath. Hydrochloric acid (95 mL, 37%) is added followed by a solution of 14 g of sodium nitrite. After stirring for ten minutes with a slight excess of nitrite present, the excess is removed with sulfamic acid. The diazonium salt solution is neutralized to pH 6 by sifting in 28 g of sodium bicarbonate at 0° C. During 15 minutes, 25.2 g of sodium sulfite is sifted in, and the pH rises to 9.4. To the bright orange colored solution, after 30 minutes and at <5° C., is added 22 g sodium bisulfite during 10 minutes. The solution is pale yellow and diazo nearly disappears. Colorless crystalline precipitate begins to form. The reaction is then stirred an additional two hours, heated to 75° C. and 70 g 37% hydrochloric acid is added. The temperature is increased to 90°–95° C. and held for four hours with sulfur dioxide evolving. The solution is stirred and cooled overnight. Sodium hydroxide (55 g, 50%) is added to pH 6. Ethyl acetoacetate Upon cooling the solution is filtered from salt, which separates. The filtrate is neutralized with acetic acid to pH 6. Pink tar separates and is isolated by decanting. It redissolves readily in water at pH 7 as a ale ink solution, useful as a coupler for making cationic azo dyes. $Y_1$ is defined as in Example 2.

20

EXAMPLE 4

The yellow dye having the structure:

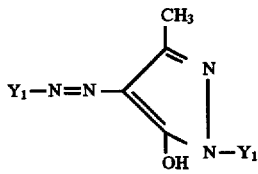

is prepared by diazotizing 0.05 g mole of the intermediate from Example 1, as in Example 2, and adding the diazonium salt solution to a solution of 0.05 mole of pyrazolone coupler prepared as in Example 3. The pH of the coupling mixture is slowly raised to 10. At pH 8 to 10, the product, a yellow monoazo dye intermediate, is completely precipitated. It redissolves completely at pH 12. Methylation by addition of two equivalents of dimethyl sulfate and subsequent neutralization to pH 7, gives a solution of bright yellow cationic dye suitable for use in making inks for ink-jet printing, the prints having very good wet-fastness on paper.

EXAMPLE 5

Synthesis of the dye intermediate having the structure

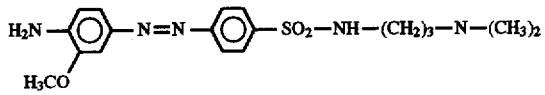

Intermediate prepared as in Example 1 (0.2 mole, 51.5 g) is dissolved a diazotized as described in Example 3. The pH of the diazo is raised to 4.0 adding 16 g sodium bicarbonate at 0° C. A solution of 0.21 mole of anisidinomethanesulfonic acid (prepared by reaction of formaldehyde-bisulfite adduct with o-anisidine in known manner) is added keeping the pH at 4–5 by adding 24 g sodium bicarbonate and temperature at 0°–5° C. After stirring for 16 hours the diazo is all coupled. The pH is raised to it by adding 40 g sodium hydroxide (50%). Solid sodium hydroxide (45 g) is added to the solution and the reaction heated at 90°–95° C. for one hour. A tarry brown precipitate forms, which is isolated after cooling and redissolved in water at 800 mL volume. Salting 15% on volume with sodium chloride and stirring gives a crystalline product, which is filtered. The cake is redissolved in water, the pH raised to 11, Darco (<100 mesh, 39) and Filtercel (4 g) added, and the solution filtered. This intermediate is useful for preparing cationic yellow dyes.

EXAMPLE 6

Preparation of bis-cationic yellow dye having the structure:

$Y_1-N=N-$ [benzene ring with OCH$_3$] $-NH-$ [triazine ring with two N] substituted with $-N(CH_3)-CH_2CH_2-\overset{\oplus}{N}(CH_3)_2-CH_2CH_2OH$ and $-NH-(CH_2)_2-\overset{\oplus}{N}(CH_3)(C_2H_5)_2$ is prepared by reaction in usual manner of the intermediate prepared in Example 5 with cyanuric chloride; and the resultant product is reacted sequentially with N'-(2-diethylaminoethylamine, aminoethylethanotamine, and dimethyl sulfate. The dye is suitable for preparation of yellow inks for ink-jet printing, the prints obtained having excellent light- and wet-fastness properties. $Y_1$ is defined as in Example 2.

EXAMPLE 7

Preparation of yellow bis-cationic dye having the structure:

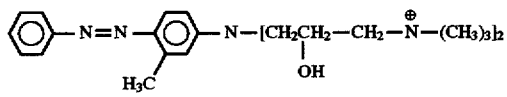

m-Toluidine (0.1 mole, 10.83 g), 3-chloro-2-hydroxypropyl-trimethylammonium chloride (66 g), isopropanol (60 g) and 25 g sodium carbonate were heated together under reflux for 3 hours until evolution of carbon dioxide stopped. The solution is filtered from inorganic salts, 100 mL of water added to the filtrate, and the isopropanol removed by distillation at reduced pressure. The resultant solution (107.5 g) is useful in preparing dyes having two pendant cationic groups which confer high solubility and excellent wet-fastness properties.

Aniline (0.05 mole) is diazotized in the conventional manner and added to 59 g of the solution of the intermediate prepared above which is iced to 0° C. The pH of the coupling is raised slowly to 6.1 by sifting in, with good stirring, 7 g of sodium bicarbonate. After stirring for some hours, the diazo is all gone, and the reaction is a reddish-yellow solution (262 g) containing about 8.5% solids. This is subjected to ultrafiltration, to remove inorganic salts. It is found useful for preparation of yellow inks for ink-jet printing, the prints having excellent wet-fastness and good light fastness properties.

In this example when the m-toluidine is replaced with an equivalent amount of aniline, otherwise proceeding in a similar manner, a yellow cationic dye is obtained having similar properties. Also, when the m-toluidine is replaced with an equivalent amount of o-anisidine, otherwise proceeding in a similar manner, a yellow cationic dye is obtained having similar properties.

When, in this example, the diazotized aniline is replaced with a molar equivalent amount of, for example, another aromatic amine such as o-, -m, or p-toluidine, o-, or p-anisidine, o-or p-phenetidine, m-chloroaniline, etc.,yellow dyes are obtained having similar properties

EXAMPLE 8

Preparation of yellow cationic dye having the structure:

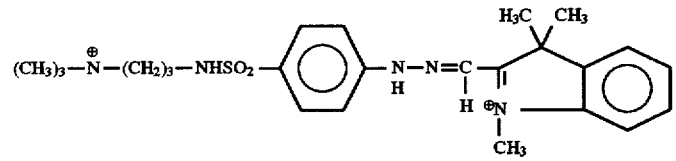

N'-(3-dimethylaminopropyl)-sulfanilamide (0.025 mole) is diazotized according to the procedure given in Example 2. To the diazonium salt solution is added dropwise 4.2 g of Fischer's Base (i.e., 2,3,3-trimethylindolenine) dissolved in 10 g acetic acid. The coupling is stirred for one hour, then neutralized slowly, first with 7 g sodium bicarbonate, then with 12% sodium hydroxide solution to raise the pH finally to 11.5. The yellow, water-soluble product tars out, and is isolated by decanting the aqueous layer. The residue is dissolved in 100 mL of deionized water, treated with Darco and Filtercel and clarified. To the filtrate is added 7 g dimethyl sulfate. The pH is kept at about 6–7, until the pH stabilized, using 11.5 mL 12% sodium hydroxide. The reaction is stirred for 16 hours (pH 6.5) giving approximately 5.5% bright yellow solution of the cationic dye, which is useful for making yellow inks for ink-jet printing, the prints having good wet-fastness.

EXAMPLE 9

0.01125 mol C.I. Reactive Red 180 (purified for ink-jet use) is dissolved in 250 mL of de-ionized water. 0.01125 mol diethanolamine is then added dropwise. After addition, the temperature of the mixture is raised to 50° C., and the pH of the mixture is kept at 7.5 by dropping in 2N NaOH. The reaction is carried out under these conditions for 18 hours, then cooled to room temperature. Dropwise addition of an equimolar amount of dimethyl sulfate while keeping the pH at 7–8 by addition of 2N NaOH resulted in methylation of the N atoms to form quaternary N groups.

A dye of the following structure results:

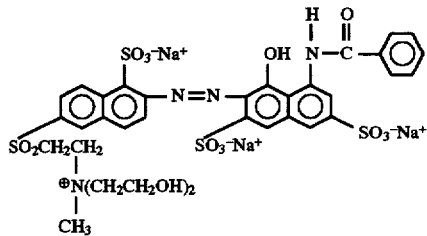

EXAMPLE 10

Example 10 was conducted in a manner similar to the one described in Example 9, except that 2-(2-aminoethylamino) ethanol was used in lieu of diethanolamine.

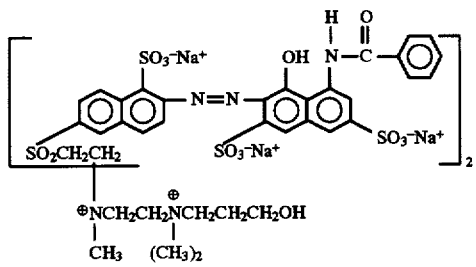

EXAMPLE 11

Example 11 was conducted in a manner similar to the one described in Example 9, except that 4-Aminomorpholine was used in lieu of diethanolamine.

A dye of the following structure results:

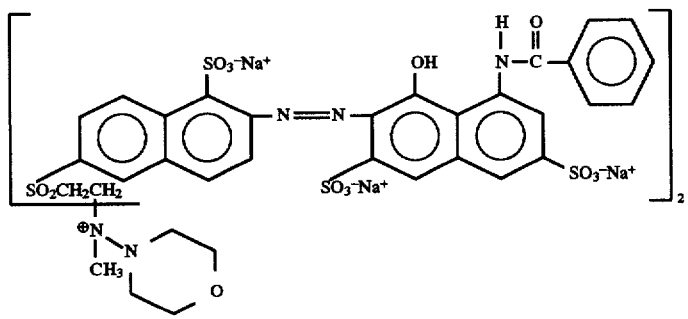

EXAMPLE 12

Example 12 was conducted in a manner similar to the one described in Example 9 except that 4-(2-aminoethyl) morpholine was used in lieu of diethanolamine.

A dye of the following structure results:

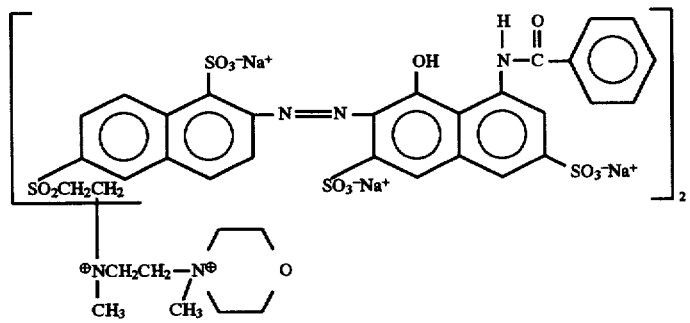

EXAMPLE 13

Example 13 was conducted in a manner similar to the one described in Example 19 except that 2-aminopyrimidine was used in lieu of diethanolamine.

A dye of the following structure results:

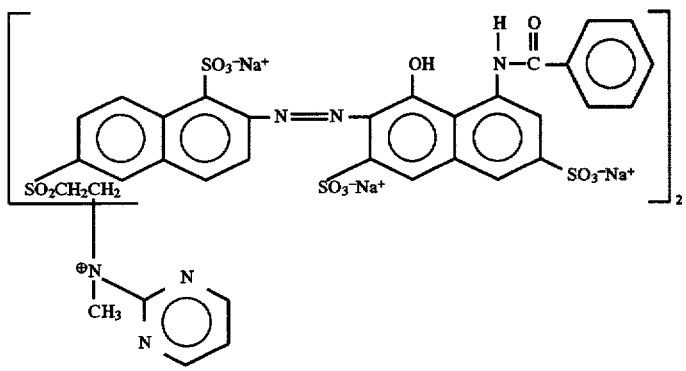

EXAMPLE 14

Example 14 was conducted in a manner similar to the one described in Example 9 except that aminopyrazine was used in lieu of diethanolamine.

A dye of the following structure results:

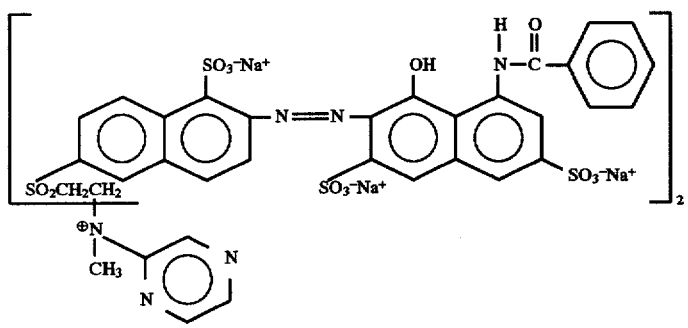

EXAMPLE 15

Example 15 was conducted in a manner similar to the one described in Example 9 except that 3-dimethylaminopropylamine was used in lieu of diethanolamine.

A dye of the following structure results:

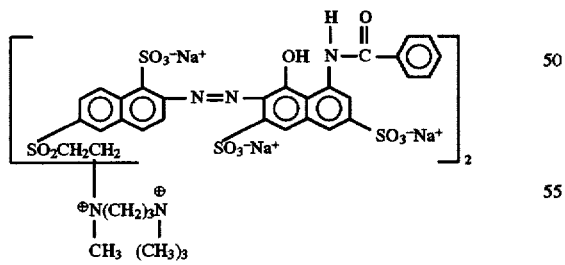

EXAMPLE 16

Example 16 was conducted in a manner similar to the one described in Example 9 except that 4-amino-1, 2, 4-triazole was used in lieu of diethanolamine.

A dye of the following structure results:

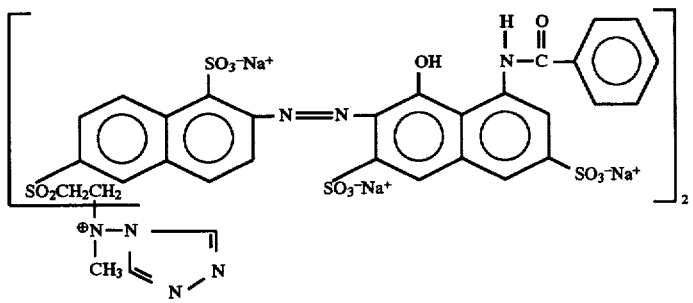

EXAMPLE 17

Example 17 was conducted in a manner similar to the one described in Example 9 except that ethanolamine was used in lieu of diethanolamine.

A dye of the following structure results:

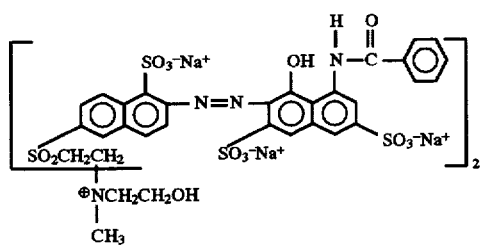

EXAMPLE 18

0.01125 mol C.I. Reactive Yellow 2 (purified for ink-jet use) is dissolved in 250 mL of deionized water, 0.01125 mol Diethylaminoethylamine is added dropwise. After addition, the temperature of the mixture is raised to 70° C., and the pH of the mixture is kept at 8 by dropping in 2N NaOH. The reaction is carried out under these conditions for 18 hours, then cooled to room temperature. Dropwise addition of an equimolar amount of dimethyl sulfate while keeping the pH at 7–8 by addition of 2N NaOH alkylates the N atoms to form quarternary N groups.

A dye of the following structure results:

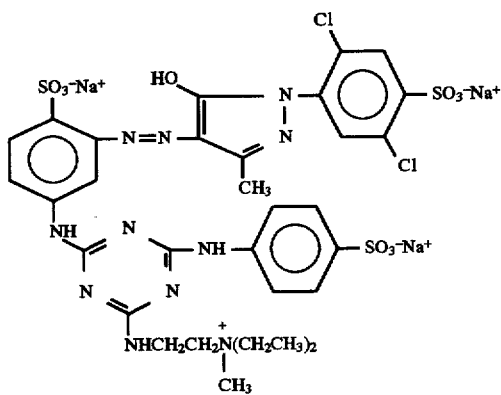

EXAMPLE 19

0.01125 mol C.I. Reactive Yellow 2 (purified for ink-jet use) is dissolved in 250 mL of deionized water, 0.01125 mol 2-(2-Aminoethylamino)ethanol is added dropwise. After addition, the temperature of the mixture is raised to 70° C., and the pH of the mixture is kept at 8 by dropping in 2N NaOH. The reaction is carried out under these conditions for 18 hours, then cooled to room temperature. No further purification is needed.

Methylation with dimethyl sulfate is believed to result in a dye of the following structure:

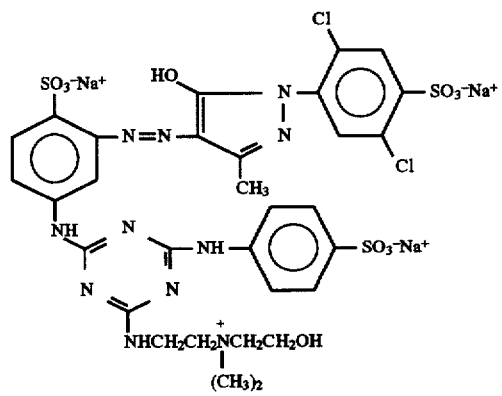

EXAMPLE 20

Example 20 was conducted in a manner similar to the one described in Example 18 except that 1-(2-hydroxyethyl) piperazine was used in lieu of diethylaminoethylamine.

A dye of the following structure results:

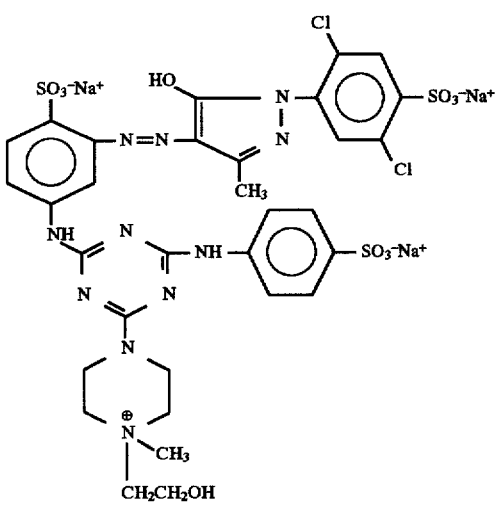

EXAMPLE 21

Copper phthalocyanine (11.5 g, 0.019 moles) [PC] is chlorosulfonated in a known manner. (cf. The Chemistry of Synthetic Dyes, vol. VI, pp. 312-323; K. Venkataraman, Ed., Academic Press, New York and London, 1972). After drown-out and icing, the paste of copper phthalocyanine tetrasulfonyl chloride (73 g) is repasted with 200 g of ice.

N,N-Diethylethylenediamine (9.3 g, 0.079 moles) is mixed with 50 g of ice, and is stirred well. The paste of CPC tetrasulfonyl chloride is added in a thin stream. The mixture is stirred 16 hours during which the pH drops from 12 to 8. The precipitated product is filtered. The filter cake is redissolved in 50 mL deionized water and sufficient 2N sodium hydroxide to give complete solution at a pH of 10-11. Dimethyl sulfate (10 g, 0.079 moles) is then added dropwise at pH of 10. The pH is maintained by adding 2N sodium hydroxide as required with stirring. After the pH has stabilized at 10, the solution is purified by ultrafiltration. The product is believed to have the structure:

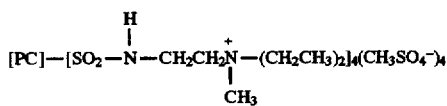

EXAMPLE 22

Using the method of Example 21, but substituting an equimolar amount of 3-Dimethylaminopropylamine in place of the N,N-diethylethylene diamine, the following dye molecule is produced:

EXAMPLE 23

A first ink of the following composition was made using a commercial basic dye, C.I. Basic Yellow 45, as the flocculating dye (all percentages are by weight):

2% Basic Yellow 45
15% 2,2,-Thiodiethanol
6% 1,2-Hexanediol
0.1% Proxel GXL
76.9% DI Water The components were added together and stirred thoroughly. The pH was maintained at 5 by adding glycolic acid and/or NAOH.

EXAMPLE 24

A second ink having a polymeric dispersant comprising in its backbone the general formula (referred to hereinafter as terpolymer L):

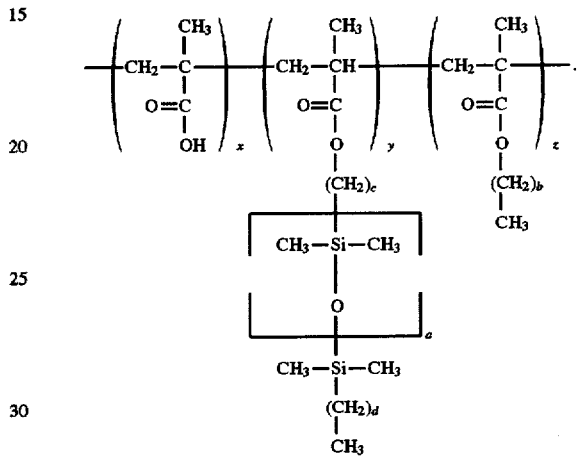

Terpolymer L is made as follows: A solution of methacrylic acid 22.8 g (265 mmol), monomethacryloxypropyl-terminated polydimethylsiloxane (PDMS-MA) 7.84 g (8.7 mmol, MW 900), stearyl methacrylate 2.95 g (8.7 mmol), dodecanethiol 2.06 g (9.9 mmol), dimethyl 2,2'-azobisisobutyrate 0.64 g (2.84 mmol) and isopropyl alcohol 100 mL is degassed with argon (done by repeated partial evacuation followed by argon backfill using a Firestone Valve) then heated to 70° C. for 16 hours. The mixture is allowed to cool to room temperature and then added slowly to rapidly stirred hexane 1.0 L. The resulting solid is isolated by vacuum filtration and dried in vacuum overnight at 80° C. The yield of the reaction is about 85%. The co-polymer is characterized by proton NMR and GPC.

A stock solution of the dispersant is prepared as follows: A 400 mL beaker containing 40 g of DI water is set on a hot plate with a magnetic stirrer. Terpolymer L, 12 g, is added to the beaker while stirring, then 18 g of 20% KOH is added to the system. The mixture is heated to 50° C. for 2 hours. The pH is adjusted to 7.5, if needed, by addition of 20% KOH. DI water is then added to bring the weight of the stock solution to 100 g (12% terpolymer L).

| Preparation A | |
|---|---|
| Components | Amount |
| Carbon Black (Cabot Corp., Monarch 880) | 26.0 g |
| Terpolymer L stock solution | 54.0 g |
| DI Water | 100.0 g |

Preparation B

| Components | Amount |
| --- | --- |
| Carbon Black (Degussa Corp., Special Black 4A) | 26.0 g |
| Terpolymer L stock solution | 54.0 g |
| DI Water | 100.0 g |

Preparations A and B are made as follows. The components are premixed by mechanical stirring until there are no visible lumps. The mixture is dispersed by an attrition process using a Szegvarl attritor model 01 std with 10–12 mesh zirconium silicate shot at a speed of 700 rpm. The attrition process is typically performed for a minimum of one hour, however, longer times at controlled temperature can also be used. The terpolymer concentrate is removed from the attritor and let down, by the addition of deionized water, to a final premix percent solids of 12%.

Using the dispersion described in Preparation A, an ink composition having the following components is made:
- 4% (by weight) carbon black
- 1% terpolymer L
- 10% polyethylene glycol (MW=400)
- 10% 1,3-propanediol
- 75% DI water The ink composition is made using the following procedure:
(1) Mix DI[water, PEG and 1,3-propanediol for 20 minutes.
(2) Add the terpolymer concentrate (Preparation A) to the mixture while stirring. Continue stirring for 20 minutes.
(3) Adjust the pH of the composition to 8.3 by the addition of 20% KOH.
(4) Filter to 1.2 µm.

EXAMPLE 25

A first ink of the following composition was made using a commercial basic dye, C.I. Basic Yellow 45, as the flocculating dye and an additional cationic material, N-tallow pentamethyl propane diammonium dichloride maintained at 5" with addition of glycolic acid and/or NaOH (all percentages are by weight):
- 2% Basic Yellow 45
- 15% 2,2-Thiodiethanol
- 6% 1,2-Hexanediol
- 3% N-tallow pentamethyl propane diammonium dichloride
- 0.1% Proxel™ GXL
- 73.9% DI Water The components were added together and stirred thoroughly. The pH was maintained at 5 by adding glycolic acid and/or NaOH.

EXAMPLE 26

The first ink of Example 23 and the second ink of Example 24 are applied, side by side, using a Lexmark® ink jet printer, WinWriter150c®. Similarly, the first ink of Example 25 and the second ink of Example 24 are applied, side by side, using a Lexmark ink jet printer, WinWriter150c. As a comparison, a standard production yellow ink and a standard production black ink are applied, side by side, using a Lexmark ink jet printer, WinWriter150c. The results demonstrating the reduced bleed of the inks of the ink system of the present invention, i.e., the inks of Examples 23, 24 and 25, compared to inks standard in the industry are shown below:

Dye Set Currently Used in Production

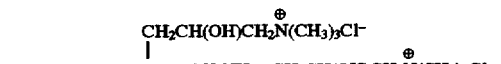

Basic Dyes Inks of Examples 23 & 24

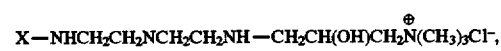

Basic Dyes with Additives Inks of Examples 24 & 25

EXAMPLE 27

A quaternary amine of the structure:

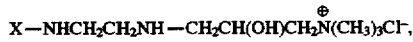

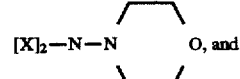

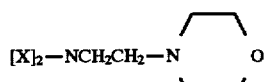

where $X = Cl^-(CH_3)_3\overset{\oplus}{N}CH_2CH(OH)CH_2$ for use as an additional cationic material were synthesized by the following method:

(3-chloro-2-hydroxypropyl)trimethylammonium chloride (47 g, 0.15 mol, 60 wt. % solution in water) is charged in a flask. Diethylenetriamine (5.21 g, 0.05 mmol) is added dropwise to the flask. The mixture is heated to 50° C., and NaOH (4N) is added dropwise to maintain the pH at 9. The solution is heated about 3 hours, until no primary amine is detected by a fluorescamine method.

The solution is cooled to room temperature and used without further purification. structure has the following formula:

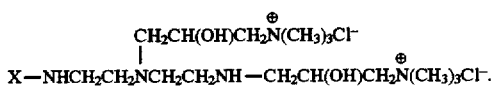

EXAMPLE 28

A quaternary amine of the structure:

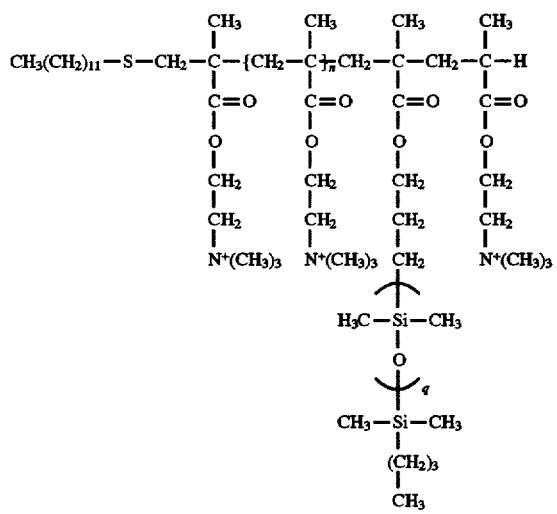

for use as an additional cationic material was synthesized by the following method:

A mixture of 2-(dimethylamino)ethyl methacrylate (22 g, 0.1 mol), monomethacryloxypropyl terminated polydimethysiloxane (15 g, 0.016 mol), dodecanethiol (2.5 g, 0.012 mol), isopropanol (100ml), and dimethyl 2,2'-azobisisobutyrate (V-601) (0.65 g, 3 mmol) is degassed with argon and then heated to 70° C. for 18 hours. The mixture is allowed to cool to room temperature, then dimethyl sulfate (12.2 g) is added dropwise to the mixture. The viscose mixture is stirred for 4 hours, then 10 g of HCl is added to it dropwise and stirred for another 2 hours. The final solution is precipitated in 600 ml hexane, filtered through vacuum and dried in a vacuum oven at 80° C. for 24 hours. Note: Stearyl methacrylate (5.88 g) can be substituted for the monomethacryloxypropyl terminated polydimethysiloxane.

In summary, numerous benefits have been described which result from employing the concepts of the invention. The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. An ink system comprising:
   a. a first ink comprising a flocculating dye in an aqueous solution; and
   b. a second ink comprising a dispersant-pigment complex in an aqueous solution, wherein the flocculating dye of said first ink is capable of flocculating the dispersant-pigment complex of said second ink.

2. The ink system of claim 1 wherein said flocculating dye comprises no anionic groups.

3. The ink system of claim 1 wherein said flocculating dye comprises at least one quarternary nitrogen.

4. The ink system of claim 1 wherein said flocculating dye is a reactive dye with a quarternary group.

5. The ink system of claim 1 wherein said flocculating dye is selected from the group consisting of anthraquinone, azo, diphenylmethane, triphenylmethane, acridine, pyran, thiopyran, indamine, azine, oxazine, thiazine, hemicyanine, azacarbocyanine, diazacarbocyanine, triazacarbocyanine and diazahemicyanine dyes.

6. The ink system of claim 1 wherein said flocculating dye is selected from the group consisting of C.I. Basic Yellow 45, C.I. Basic Blue 163, C.I. Basic Red 15, C.I. Basic Red 16 and C.I. Basic Red 49.

7. The ink system of claim 1 wherein said flocculating dye is a compound of the formula:

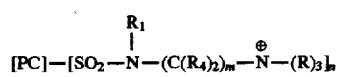

wherein m is about 0–6; n is about 2–4; each R is independently lower ($C_{1-4}$) alkyl, arylalkyl or hydroxyalkyl; PC is a metallic or nonmetallic comprising phthalocyanine group; $R_1$ is H or —$CH_3$; and each $R_4$ is independently H, lower alkyl or hydroxyalkyl.

8. The ink system of claim 7 wherein said compound is a dye selected from the group consisting of.

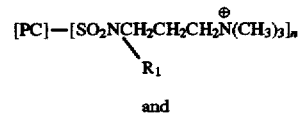

wherein $R_1$ is H or —$CH_3$ and n is about 3 or 4.

9. The ink system of claim 7 wherein said compound is a cyan dye and PC is a copper phthalocyanine group.

10. The ink system of claim 1 wherein said flocculating dye is a compound of the formula:

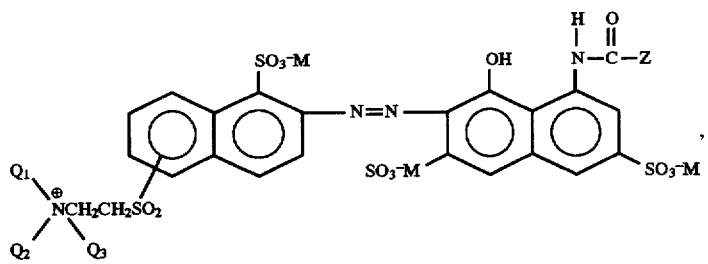
wherein $Q_1$ is hydroxyalkyl or
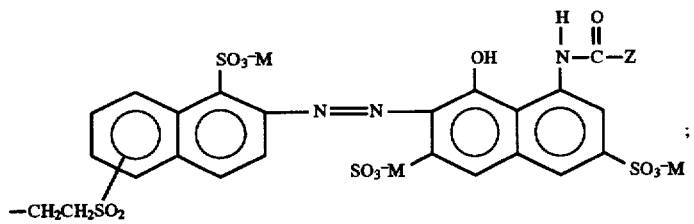
$Q_2$ is H, lower alkyl,
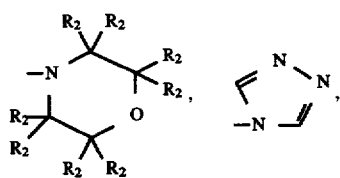
hydroxyalkyl,
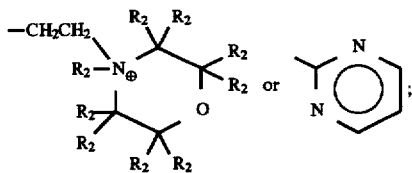
$Q_3$ is H or $(C_{1-4})$ alkyl;
each M is independently $H^+$, $Na^+$, $K^+$, $Li^+$, $N^+(R_2)_4$;
each $R_2$ is independently H, lower $(C_{1-4})$ alkyl or hydroxyalkyl Z is an aromatic, aliphatic, amine or alkoxy group.
11. The ink system of claim 10 wherein said compound is selected from the group consisting of:
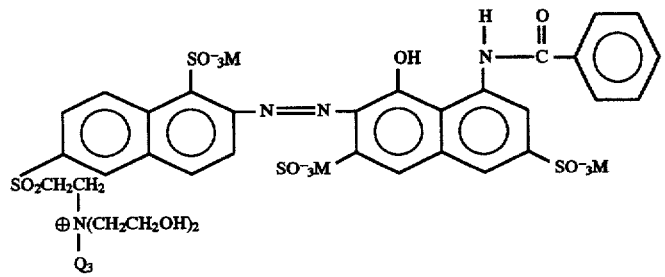
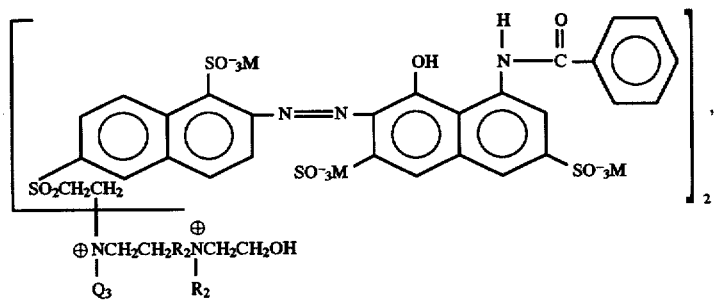

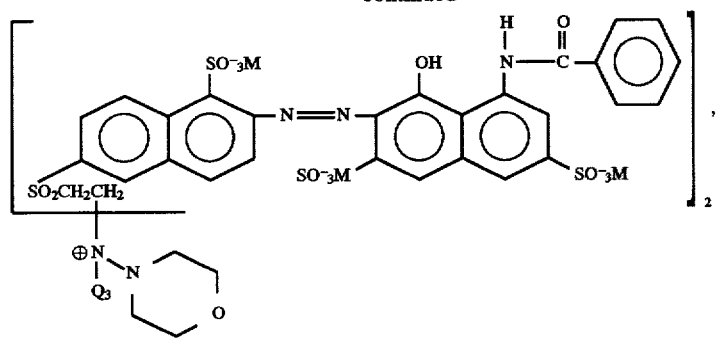,
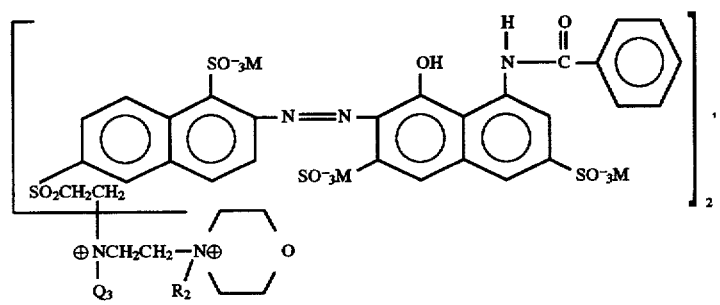,
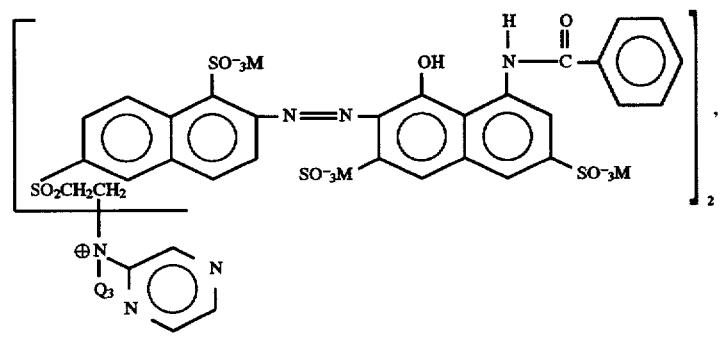,
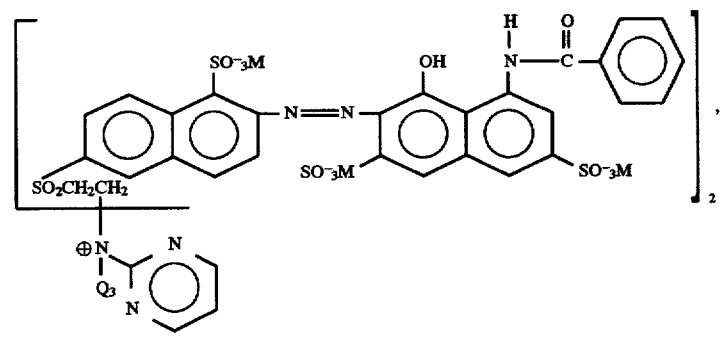,
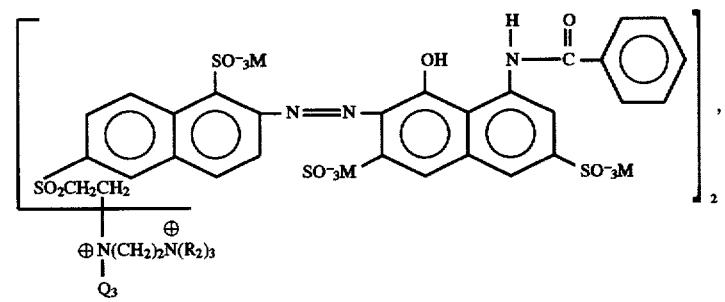,

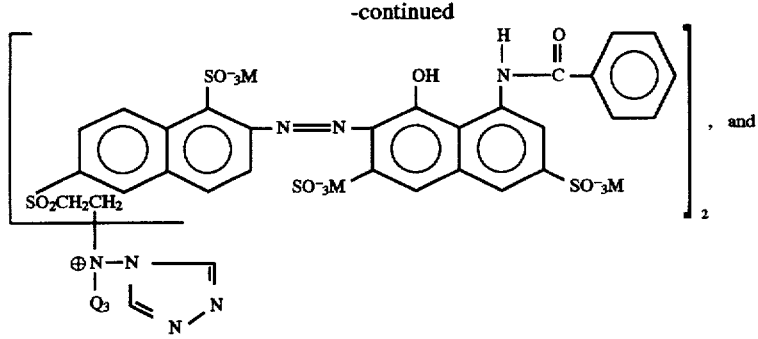
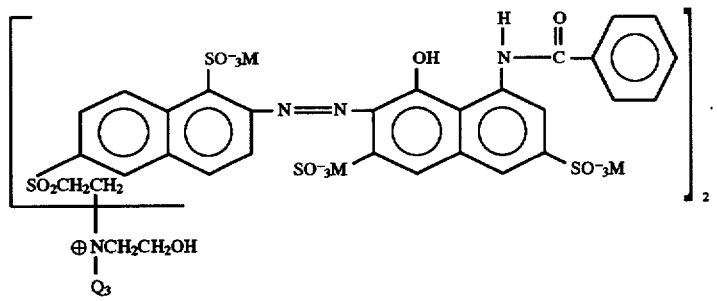
12. The ink system of claim 10 wherein said compounds are magenta dyes and $M^{\oplus}$ is $Na^{\oplus}$;
$Q_3$ is H or —$CH_3$ and $R_2$ is H or —$CH_3$.
13. The ink system of claim 1 wherein said flocculating dye compound selected from the group consisting of:
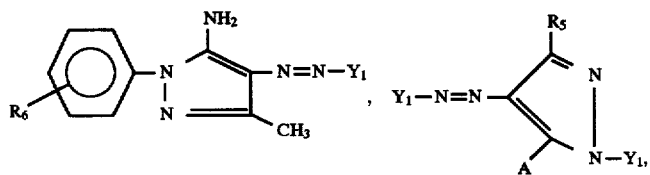
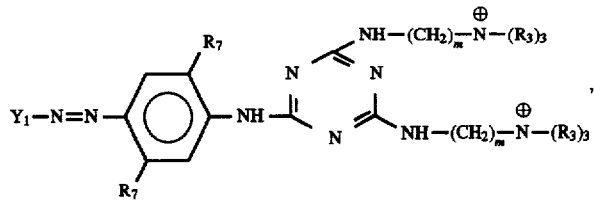
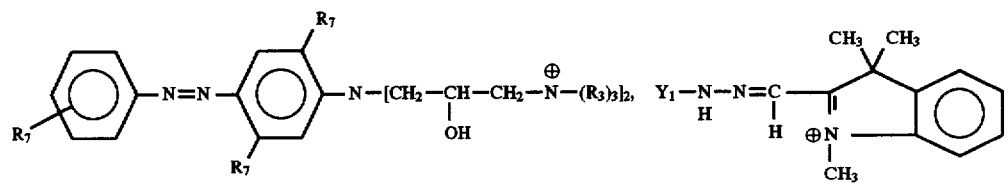

-continued
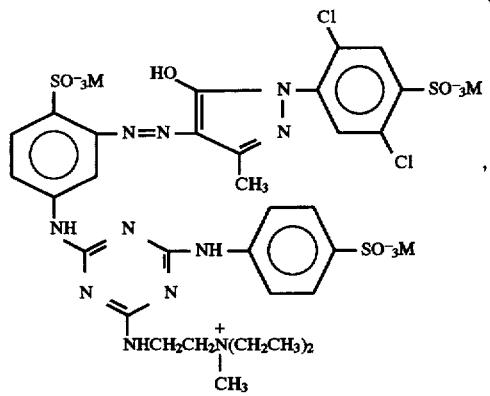
,
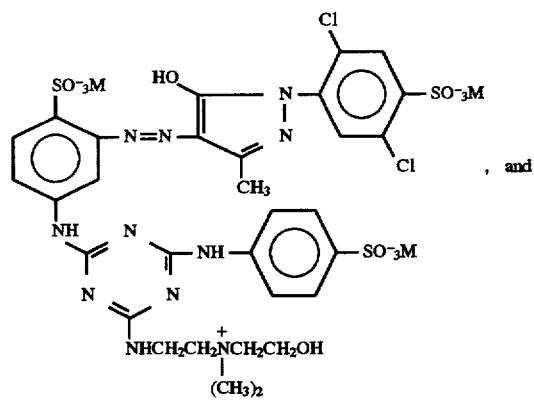
, and
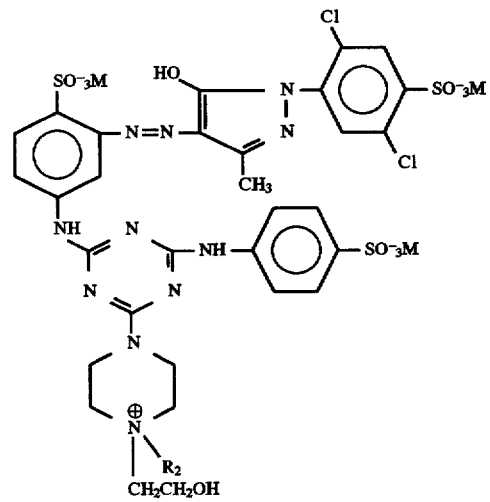
wherein m is about 0 to 6;
m' is about 0 to 6;
each R is independently lower $C_{(1-4)}$ alky, arylalky, hydroxyalkyl;
$R_5$ is lower $C_{(1-4)}$ alkyl or $CO_2M$;
$R_6$ is H, halogen, lower akyl or lower alkoxyl
each $R_7$ is independently H lower alkyl or lower alkoxyl
each $R_3$ is independently lower $C_{(1-4)}$ alkyl or hydroxyalkyl
$Y_1$ is 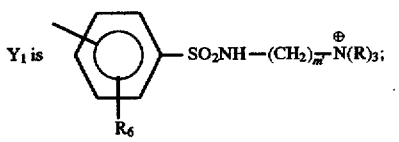
A is —OH or —$NH_2$; and
M is as previously defined.

14. The ink system of claim 1 wherein said first ink further comprises a first ink solvent comprising at least about 25% by weight water and a balance which is an organic solvent.

15. The ink system of claim 14 wherein said first ink comprises about 1–6% by weight flocculating dye.

16. The ink system of claim 14 wherein said first ink further comprises a material selected from the group consisting of a humectant, a penetrant, an additional cationic material, a biocide and combinations thereof.

17. The ink system of claim 16 wherein said first ink about comprises 0.5–6% by weight flocculating dye, 5–25% by weight humectant, about 0.05–10% by weight penetrant, about 0–5% by weight additional cationic material and about and 0.1–0.5% by weight biocide and a balance which is solvent.

18. The ink system of claim 17 wherein said humectant is 2,2-thiodiethanol; said penetrant is 1,2-hexanediol; and said additional cationic material is a quaternary amine.

19. The ink system of claim 17 wherein said additional cationic material is selected from the group consisting of 1-dodecylpyridinium chloride; 1-hexadecylpyridinium chloride; methyldodecylbenzyltrimethyl ammonium chloride; octylcresoxyethoxyethyldimethyl benzyl ammonium chloride; lauryldimethyl benzyl ammonium chloride; ethyl bis (polyethoxylethanol)alkyl ammonium chloride; N-tallow pentamethyl propane diammonium dichloride; cocoaldylmethyl [ethoxylated (2)] chloride; tallowalkylethoxylated (3) acetates; N-hexadecyl-N,N,N-trimethylammonium chloride; and N,N-dimethyl-2-hydroxypropylammonium chloride and combinations thereof.

20. The ink system of claim 17 wherein said additional cationic material is selected from the group consisting of:

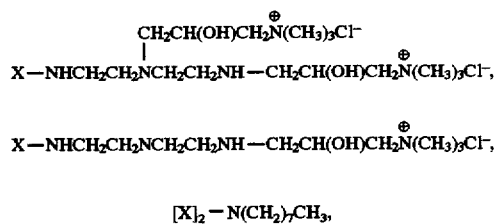

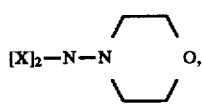

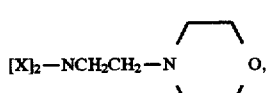

wherein X is $Cl^-(CH_3)_3N^{\oplus}CH_2CH(OH)CH_2$,

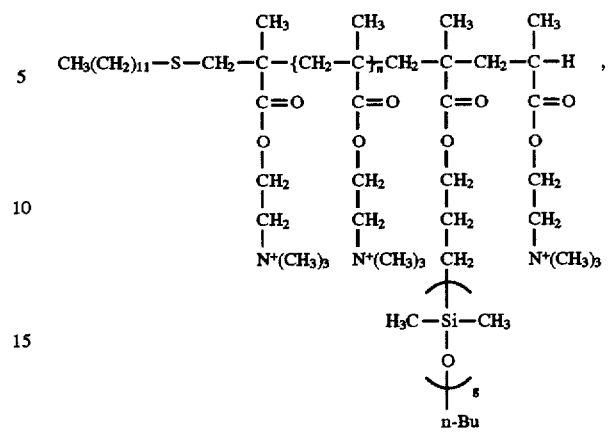

and

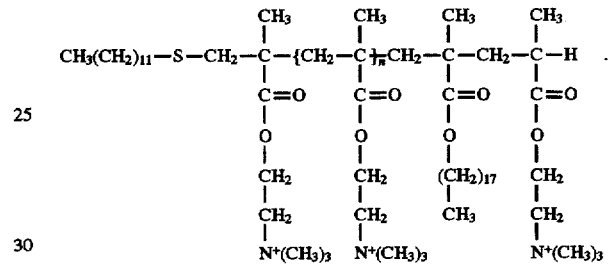

21. The ink system of claim 1 wherein said first ink has a pH less than 7.

22. The ink system of claim 1 wherein said first ink has a pH between about 4 and about 6.

23. The ink system of claim 1 wherein said second ink comprises 1.5–12% by weight dispersant-pigment complex.

24. The ink system of claim 23 wherein said dispersant is a polymeric dispersant comprising a hydrophilic polymeric segment and a hydrophobic polymeric segment.

25. The ink system of claim 24 wherein said dispersant comprises a stabilizing segment.

26. The ink system of claim 25 wherein said dispersant is selected from the group consisting of graft copolymers, block copolymers and terpolymers.

27. The ink system of claim 23 wherein said second ink comprises about 0.1–10% by weight pigment.

28. The ink system of claim 23 wherein said pigment is selected from the group consisting of azo pigments, polycyclic pigments, dye lakes, organic pigments, and inorganic pigments.

29. The ink system of claim 23 wherein said pigment is selected from the group consisting of titanium oxide, iron oxide and carbon black.

30. The ink system of claim 23 wherein said polymeric dispersant has a hydrophobia amide side chain.

31. The ink system of claim 23 wherein said second ink further comprises a second ink solvent comprising at least about 25% by weight water with a balance which is an organic solvent.

32. A method of controlling bleed between ink comprising the steps of:
  a. applying a first ink to a surface, wherein the first ink comprises a flocculating dye in an aqueous solution; and b. applying a second ink to the surface contiguous to the first ink, wherein said second ink comprises a dispersant-pigment complex in an aqueous solution, and wherein the flocculating dye of said first ink is capable of flocculating the dispersant-pigment complex of said second ink.

33. The method of claim 32 wherein said dispersant-pigment complex of said second ink comprises carbon black.

34. The method of claim 32 wherein said flocculating dye comprises no anionic groups.

35. The method of claim 32 wherein said flocculating dye comprises at least one quarternary nitrogen.

36. The method of claim 32 wherein said flocculating dye comprises a reactive dye with a quarternary group.

37. The method of claim 32 wherein said first ink comprises about 0.5–6% by weight flocculating dye, 5–25% by weight humectant, 0.05–10% by weight penetrant, 0–5% by weight additional cationic material and 0.1–0.5% by weight biocide and a balance which is solvent.

* * * * *

UNITED STATES PATENT AND TRADEMARK OFFICE
CERTIFICATE OF CORRECTION

PATENT NO : 5,735,941

DATED : April 7, 1998

INVENTOR(S) : James Feeman et al.

It is certified that error appears in the above-identified patent and that said Letters Patent is hereby corrected as shown below:

Col. 2, line 13
  replace "mine"
  with --amine--.

Col. 2, line 41
  replace "Wick ramanayake"
  with --Wickramanayake--.

Col. 2, line 63
  replace "fast"
  with --first--.

Col. 3, line 67
  replace "LE9-96-020"
  with --Serial No. 08/690,467, filed July 24, 1996--.

Col. 4, line 28
  replace "LE9-96-020"
  with --Serial No. 08/690,467, filed July 24, 1996--.

Col. 12, line 26
  replace "$R_5$"
  with --$CH_3$--.

Col. 44, line 17
  replace "g"
  with --8--.

Signed and Sealed this

Twenty-third Day of March, 1999

Attest:

Q. TODD DICKINSON

Attesting Officer

Acting Commissioner of Patents and Trademarks